US006929624B1

(12) United States Patent
Del Castillo

(10) Patent No.: US 6,929,624 B1
(45) Date of Patent: Aug. 16, 2005

(54) INTRAVENOUS CATHETER HOUSING WITH RETRACTABLE NEEDLE

(76) Inventor: Gil Del Castillo, 3333 Dominion, #721, Katy, TX (US) 77450

( * ) Notice: Subject to any disclaimer, the term of this patent is extended or adjusted under 35 U.S.C. 154(b) by 120 days.

(21) Appl. No.: 10/355,629

(22) Filed: Feb. 3, 2003

(51) Int. Cl.⁷ ............................................. A61M 5/178
(52) U.S. Cl. .............................. 604/164.12; 604/164.07
(58) Field of Search ........................... 604/159, 164.07, 604/164.12, 528, 164.06

(56) References Cited

U.S. PATENT DOCUMENTS

| | | | |
|---|---|---|---|
| 2,685,097 A | * | 8/1954 | Allen ....................... 15/104.33 |
| 3,561,445 A | | 2/1971 | Katerndahl et al. |
| 3,995,628 A | | 12/1976 | Gula et al. |
| 4,160,451 A | | 7/1979 | Chittenden |
| 4,342,313 A | | 8/1982 | Chittenden |
| 4,397,091 A | | 8/1983 | Gustavsson et al. |
| 4,637,404 A | | 1/1987 | Gessman |
| 5,810,835 A | | 9/1998 | Ryan et al. |
| 6,086,008 A | * | 7/2000 | Gray et al. .............. 242/388.6 |
| 6,093,179 A | * | 7/2000 | O'Hara et al. .............. 604/500 |
| 6,231,564 B1 | * | 5/2001 | Gambale ..................... 604/528 |
| 6,290,675 B1 | * | 9/2001 | Vujanic et al. ............. 604/159 |

* cited by examiner

Primary Examiner—Michael J. Hayes
Assistant Examiner—Sundeep Virdi
(74) Attorney, Agent, or Firm—Egbert Law Offices

(57) ABSTRACT

A catheter housing assembly having a housing, a needle assembly with a rigid portion and a flexible portion, a recoil device positioned in an interior area of the housing for coiling the flexible portion of the needle assembly therearound, and a trigger connected to the housing so as to retract the rigid portion of the needle into the interior area of the housing. The rigid portion of the needle assembly extends tangentially outwardly of the housing. The flexible portion of the needle assembly has a bead, a flexible line extending through the bead, a first rigid spacer connected to the rigid portion of the needle assembly and a plurality of additional rigid spacers interposed in jointed relationship between the bead and the first rigid spacer.

13 Claims, 3 Drawing Sheets

INTRAVENOUS CATHETER HOUSING WITH RETRACTABLE NEEDLE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to needle assemblies for use with catheters. More particularly, the present invention relates to retractable needle assemblies for preventing reuse of the needle. Additionally, the present invention relates to catheter housings which contain a retractable needle whereby the needle can be recoiled around a spool so as to retract the rigid portion of the needle subsequent to use.

BACKGROUND OF THE INVENTION

For many medical procedures, such as intravenous fluid administration, communication with the blood system of a patient is required. Ordinary, it is necessary to use an incising element, such as a rigid needle having a sharp tip, to gain access to a vein. However, it is not desirable to leave a sharp needle in place in the vein for any extended period time due to the potential damage the sharp tip may cause. Thus, a flexible conduit, such as a plastic catheter, is often inserted into the vein concurrently with a rigid needle. Since the flexible plastic catheter is concentrically positioned over (or alternatively within) the rigid needle, the needle can then be withdrawn leaving only the flexible catheter indwelling in the vein. One type of such catheter is manufactured and sold by Abbott Laboratories and is known as an ABBOCATH (TM) catheter. This ABBOCATH (TM) catheter is an indwelling intravenous catheter having a flexible catheter over a rigid withdrawable needle.

In the past a variety of U.S. patents have issued relating to various devices for the installation of catheters, for the withdrawal and retraction of needles, and for the utilization of catheters. U.S. Pat. No. 5,810,835, issued on Sep. 22, 1998 to Ryan et al., teaches a catheter insertion device having a valve. This catheter insertion device includes a catheter dispenser having a catheter outlet extending from a base and a drum receptacle engaged to the base in a rotating relationship. An inlet opening in the base is coaxially aligned with the catheter outlet. A passageway extends from the inlet opening tangentially through the catheter drum to the catheter outlet. A rigid needle is disposed through the passageway so that the sharp tip extends beyond the catheter outlet. A flexible introducer catheter generally contiguously and telescopically surrounds the distal portion of the needle. The introducer catheter extends beyond the catheter outlet to a position on the needle that is proximal to the sharp tip and is operatively associated with the needle for insertion into the vein of a patient. A one-way flow valve is in fluid-tight connection with the proximal end of the flexible introducer catheter. The valve forms a portion of the passageway so that when the needle is slidably removed from the passageway, the valve minimizes the fluid backflow from the vein. When the catheter drum is rotated relative to the base, the drum catheter is threadedly inserted into and through the one-way valve, through the indwelling flexible introducer catheter, and into the vein of the patient.

U.S. Pat. No. 4,637,404, issued on Jan. 20, 1987 to L. J. Gessman, describes a method and apparatus for converting a catheter to a cardiac pacing electrode. This device utilizes an in-place catheter having at least one lumen terminating at a distal port which is positioned within a pre-selected heart chamber. The other end of the lumen terminates in a proximal port which is connected to a cannular connector defining an adjustable seal having a distal portion of wire electrode extending therethrough.

U.S. Pat. No. 4,397,091, issued on Aug. 9, 1983 to Gustavsson et al., teaches a dispensing container for venus catheters. This container has an outlet opening for dispensing the catheter therethrough, a rotatable means for feeding the catheter out through the outlet, and an indicating means operatively connected to the feeding means for indicating the length of the catheter dispensed through the outlet.

U.S. Pat. No. 4,342,313, issued on Aug. 3, 1982 to R. M. Chittenden, describes a catheter insertion device having a drum-like receptacle which advances the catheter when it is rotated relative to the base so as to cause the catheter to move through a tubular outlet. A removable needle extends coaxially through a tubular housing tangentially affixed to the dispenser. A flexible cannula telescopically surrounds the distal portion of the needle. The cannula is adapted to a catheter outlet from the receptacle and is adapted to be inserted into the vein of a patient during venipuncture. Once venipuncture is performed, the needle is slidably removed from the cannula and catheter outlet. The catheter is telescopically inserted into and through the cannula and thereby into the vein of the patient. The base and receptacle may then be easily separated and removed from the catheter.

U.S. Pat. No. 4,160,451, issued on Jul. 10, 1979 also to R. M. Chittende, describes a unidirectional, needle outside, reel-type catheter placement unit. The catheter placement unit includes an overcap or cover which is only coupled to the reel of the reel-type catheter placement unit by a ball clutch when the overcap is rotated in a direction that advances the catheter from the unit.

U.S. Pat. No. 3,995,628, issued on Dec. 7, 1976 to Gula et al., describes another type of catheter insertion device. This device utilizes a catheter that is wound inside a two-piece generally cylindrical dispenser and extends outwardly into a slotted needle secured to an outlet from the dispenser. A stiffener is used which comprises a closely-wound wire helix which surrounds a central straight wire and is positioned inside the catheter. The dispenser includes two relatively rotatable parts, one a relatively flat base with a slot communicating with the slotted needle, and the other a receptacle having an inwardly-facing wall which engages the catheter. The receptacle is releasably and rotatably held to the base by a central spindle extending upwardly from the base member through a hole in the top of the receptacle. A flexible feed guide extends from the base adjacent to the dispenser outlet and guides the catheter toward the outlet. The guide is engageable with a stop to positively prevent further rotation of the receptacle at a predetermined point when the proximal end of the catheter nears the outlet.

U.S. Pat. No. 3,561,445, issued on Feb. 9, 1971 to Katerndahl et al., teaches another type of catheter placement unit designed to advance a catheter in a sterile state. This device includes a catheter having a hub, a concentric needle and hub, a sheath, and a catheter container adapted to enclose a relatively long catheter and adapted to advance the catheter from the container through the needle and sheath without exposing the catheter.

It is an object of the present invention to provide a catheter housing assembly which shortens the overall length of the handle portion of the IV catheter so as to provide better control and a better angle of penetration.

It is another object of the present invention to provide a catheter housing assembly which automatically retracts the needle back into the housing and prevents reuse of the needle.

It is an object of the present invention to provide a catheter housing assembly which can easily fit between the thumb and index finger of the user.

It is still a further object of the present invention to provide a catheter housing assembly which easily and automatically retracts the needle subsequent to use.

These and other objects and advantages of the present invention will become apparent from a reading of the attached specification and appended claims.

BRIEF SUMMARY OF THE INVENTION

The present invention is a catheter housing assembly that comprises a housing, a needle assembly having a rigid portion and a flexible portion, a recoil means positioned within the interior area of the housing, and a trigger means connected to the housing so as to be cooperative with the needle assembly. The housing has a generally rounded area and an outlet extension extending outwardly from the round area. The recoil means is for coiling the flexible portion of the needle assembly therearound. The trigger means is cooperative with the needle assembly so as to actuate the recoil means for retracting the rigid portion of the needle assembly into the interior area of the housing as the flexible portion of the needle assembly is coiled around the recoil means.

The rigid portion of the needle assembly has an extended position extending outwardly of the outlet extension of the housing. This rigid portion of the needle assembly extends in generally tangential relationship to the rounded area of the housing when in the extended position. This rigid portion of the needle assembly has a length of approximately two inches. The housing at the area of the outlet extension has a length of also approximately two inches. The flexible portion has one end connected to an end of a rigid portion. This flexible portion has an opposite end connected to the recoil means.

In the present invention, the flexible portion of the needle assembly comprises a bead, a flexible line connected to the recoil means and extending through the bead, a first rigid spacer member affixed to the end of the rigid portion of the needle assembly, and a plurality of additional rigid spacers interposed in jointed relationship between the first rigid spacer and the bead. The flexible line can either be a cord, a nylon line or a wire.

In the present invention, the trigger means is a slide member. This slide member captures the bead of the flexible portion of the needle assembly. The trigger means is for releasing the bead as to cause the recoil means to retract the flexible portion of the needle assembly. The slide member is positioned in an outlet extension of the housing. This slide member has a portion extending outwardly of the housing so as to be movable by an index finger of a person holding the housing. The housing has a size suitable for fitting between a thumb and an index finger of a human being.

In the present invention, the recoil means comprises a spool rotatably positioned in the interior area of the rounded area of the housing, and a constant force spring cooperative with the spool so as to urge the spool to rotate in a single direction for coiling the flexible portion of the needle assembly therearound.

DETAILED DESCRIPTION OF THE INVENTION

Figure 1:
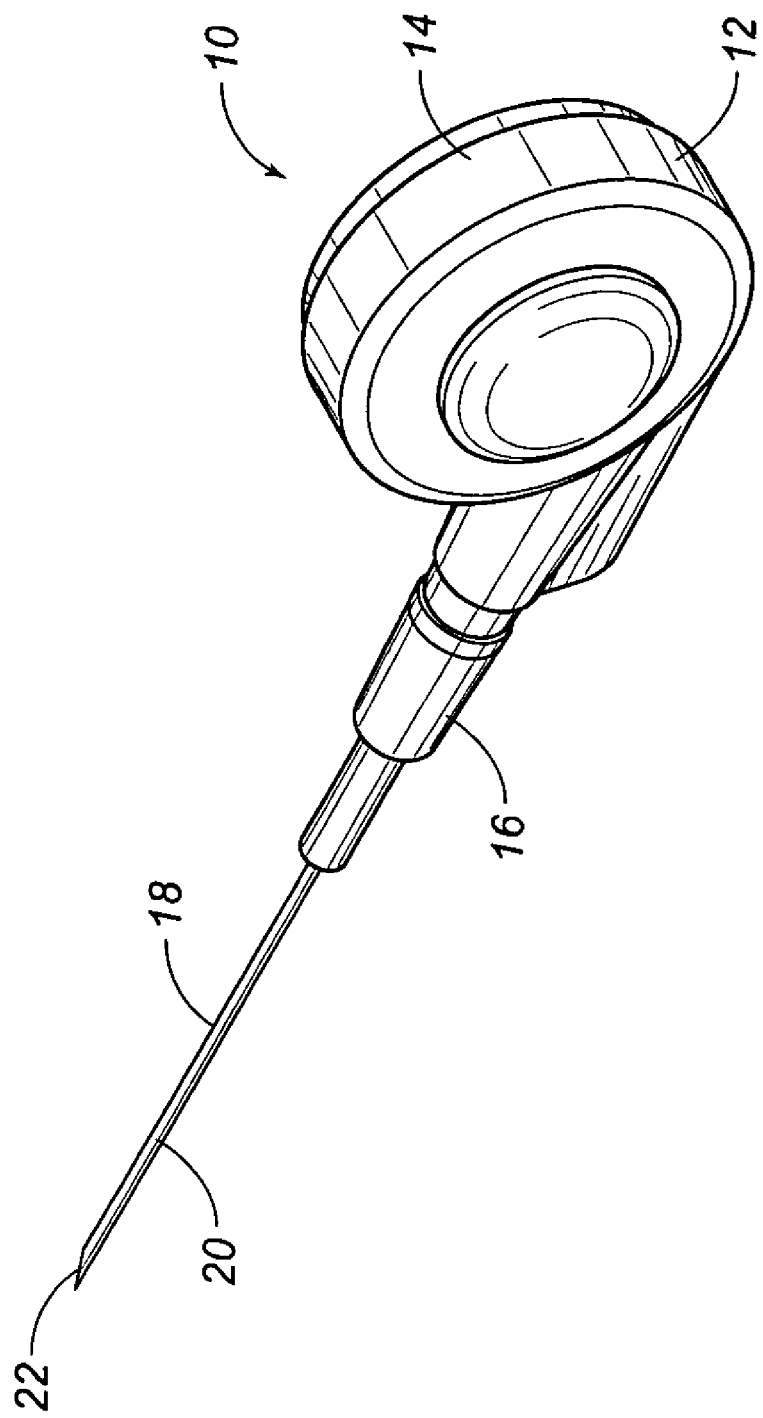
FIG. 1 is a perspective view of the catheter housing assembly of the present invention.

Referring to FIG. 1, there is shown the catheter housing assembly 10 in accordance with the teachings of the preferred embodiment of the present invention. The catheter housing assembly 10 include a housing 12 having a generally rounded area 14 and an outlet extension 16 extending outwardly of the rounded area 14. The housing 12 has a suitable interior area. A needle assembly 18 extends outwardly of the outlet extension 16 of the housing 12. The needle assembly 18 has a rigid portion 20 extending outwardly of the outlet extension 16 and a sharp end 22 opposite the outlet extension 16 and the housing 12.

In the present invention, the housing 12 is particularly configured so as to shorten the overall length of the handle portion of the IV catheter so as to allow better control and a more suitable angle penetration. The housing 12 is designed to fit between the thumb and index finger of a human being so as to allow a better angle in which to insert the IV needle. The assembly 10 is designed so that no part of the housing 12 would protrude into the palm area of the hand. This allows better control without restricted movement caused by an extended length.

Importantly, so as to facilitate the proper control and better angle of penetration, it can be seen that the outlet extension 16 extends outwardly of the rounded area 14 of housing 12 generally tangentially. Similarly, the needle assembly 18 will also extend through the generally tangential angle with respect to the rounded area 14 of housing 12. The rigid portion 20 of the needle assembly 18 should have a length of approximately two inches. Similarly, the length of the housing 12 at the outlet extension 16 will also have a length of approximately two inches. As a result, when the rigid portion 20 of needle assembly 18 is retracted into the interior area of the housing 12, the sharp end 22 will reside within the outlet extension or within the interior area of the housing 12.

Figure 2:
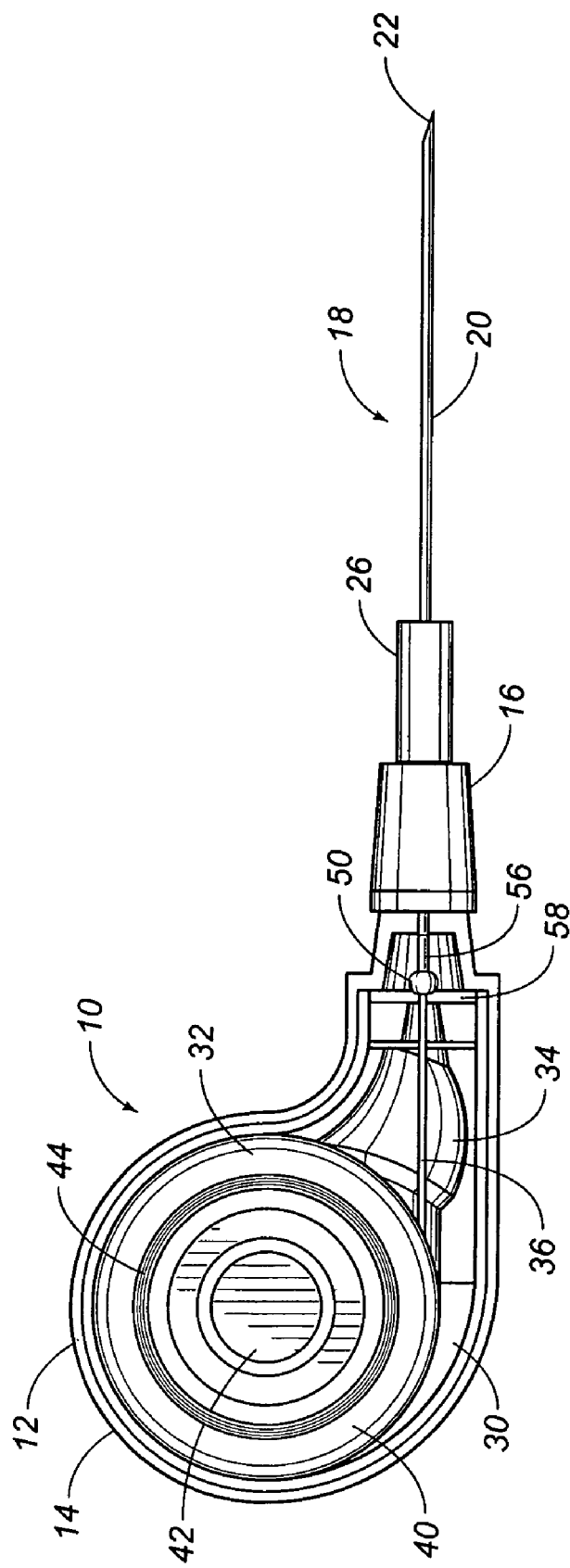
FIG. 2 is an interior view of the catheter housing assembly of the present invention.

Referring to FIG. 2, the details of the mechanism associated with the housing assembly 10 of the present invention are illustrated. In FIG. 2, the housing assembly 12 shows rounded area 14 and the outlet extension 16. The rigid portion 20 of the needle assembly 18 is shown as extending outwardly of the end 26 of the outlet extension 16. The sharp end 22 of the needle assembly 18 is opposite to the housing 12. It can be seen in FIG. 2 that the rigid portion 20 of the needle assembly 18 extends in generally tangential relationship to the rounded area 14 of housing 12.

The housing 12 defines an interior area 30 therein. The interior area 30 will accommodate a recoil means 32 and a trigger means 34 therein. The recoil means is for coiling the flexible portion 36 of needle assembly 18 therearound. The trigger means 34 is for actuating the recoil means 32 so as to retract the rigid portion 20 of the needle assembly 18 into the interior area 30 of the housing 12 as the flexible portion 36 of the needle assembly 18 is coiled around the recoil means 32.

In the present invention, the recoil means 32 comprises a spool 40 rotatably mounted about axle 42 within the interior area 30 of housing 12. A constant force spring 44 engages the spool 20 in relation to the axle 42 so as to urge the spool 40 in a single direction of rotation. The flexible portion 36 of the needle assembly 18 is affixed to the spool 32. When the trigger means 34 is actuated, the constant force spring 44 will act on the spool 32 so as to cause the spool 32 to rotate and to draw the flexible portion 36 therearound and to retract the rigid portion 20 of needle assembly 18 back into the interior area 30 of housing 12. It is important to note that the recoil means of the present invention is related to various prior art items. In particular, this recoil means operates similar to the recoil mechanisms associated within a tape measure. When a suitable trigger is pushed, the recoil means will automatically carry out a retracting motion in a fast and efficient manner. It is important to note that, within the concept of the present invention, various other mechanisms (other than the spool and constant force spring mechanism) can be utilized within the concept of the present invention. It is important to the concept of the present invention that the retraction of the rigid portion 20 of the needle assembly 18 be carried out in an efficient and automatic manner.

In the present invention, the flexible portion 36 of the needle assembly 18 can be a flexible line, such as a length of cord, a length of nylon line, or a length of wire. The end of the flexible portion 36 will be affixed to the end of the rigid portion 20 of needle assembly 18 opposite end the sharp end 22. This flexible portion will extend through a bead 50 located in proximity to the trigger means 34. A plurality of rigid spacers 56 are interposed between the bead 50 and the end of the rigid portion 20 of needle assembly 18. This plurality form spacer members will reside in a generally jointed relationship so as to provide a rigid force to the rigid portion 20 of needle assembly 18 during puncture and use while also allowing the flexible portion 36 of the needle assembly 18 to wrap around the spool 40 when the recoil means 32 is actuated.

The trigger means 34 includes a slide member 58 which is positioned on the forward side of the rounded area 14 of housing 12. The slide member 58 captures the bead 50 so as to hold the needle assembly 18 with the rigid portion 20 in an extended position. By sliding the slide member 58 upwardly with the index finger, and by controlling the position of the housing 12 with the thumb and middle finger, the bead 50 will be released so as to and allow the rigid portion 20 of needle assembly 18 to retract into the interior area 30 of the housing 12. The plurality of spacer members 56 and the bead 50, that are placed behind the rigid portion 20 of needle assembly 18, will allow the needle assembly 18 to retract into the shorter housing by wrapping around the spool 40 in the rounded area 14. Subsequent to retraction, the housing 12 can be removed from the catheter luer taper so as to leave the catheter in the patient's vein. Once triggered, the needle assembly 18 cannot be moved back into its extended position for reuse.

Figure 3:
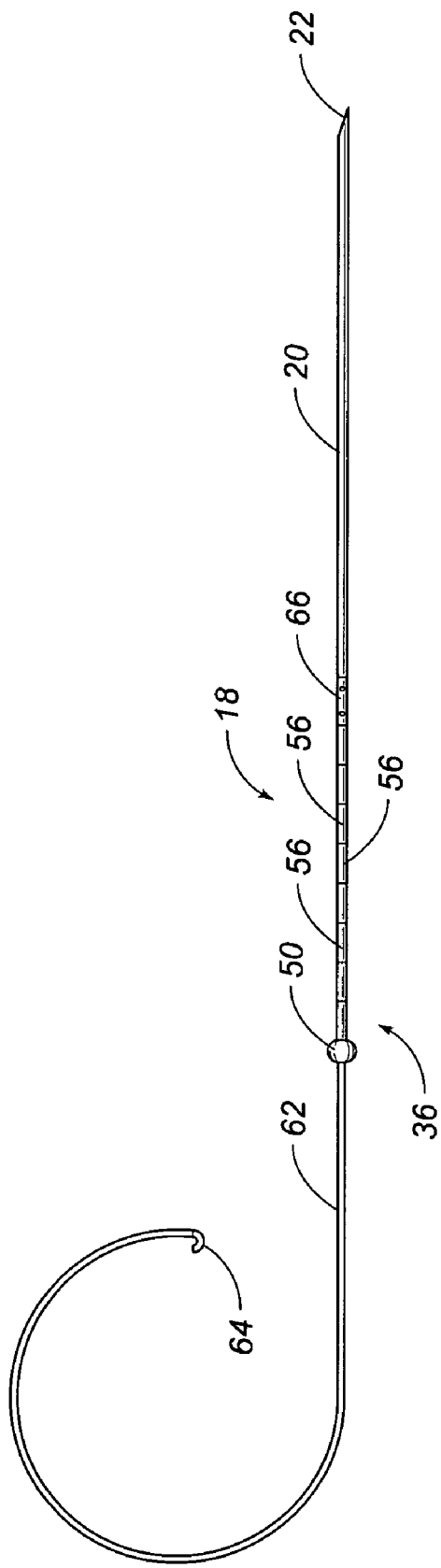
FIG. 3 is an isolated view of the needle assembly of the present invention.

FIG. 3 is an isolated view of the needle assembly 18 of the present invention. The needle assembly 18 includes the rigid portion 20 and the flexible portion 36. The rigid portion 20 is a longitudinal member having sharp end 22 at an end thereof. The flexible portion 36 includes the bead 50, a flexible line 62 having an end 64 connected to the recoil means 32, a first rigid spacer member 66 affixed to the opposite end of the rigid portion 20 from the sharp end 22, and a plurality of additional rigid spacers 56 extending in end-to-end relationship between the bead 50 and the spacer 66. The first rigid spacer member 66 is suitably crimped onto the end of the rigid portion 20. Each of the plurality of additional rigid spacers 56 are arranged in unconnected end-to-end relationship so as to extend in a relatively "jointed" manner. The flexible line 62 extends through the interior of the bead 50 and through the spacers 56 and 66 so as to be affixed to the end of the rigid portion 20. In this manner, the rigid spacers 56 and 66 provide rigidity to the needle assembly 18, when desired, while also providing flexibility for the purpose of wrapping the flexible portion 36 around the spool 40 of the recoil means 32.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:
1. A catheter housing assembly comprising:
a housing having a generally rounded area and having an outlet extension extending outwardly of said rounded area, said housing having an interior area;
a needle assembly having a rigid portion and a flexible portion;
a recoil means positioned in said interior area of said housing, said recoil means for coiling said flexible portion of said needle assembly therearound; and
a trigger means connected to said housing and cooperative with said needle assembly so as to actuate said recoil means for retracting said rigid portion of said needle assembly into said interior area of said housing as said flexible portion of said needle assembly is coiled by said recoil means, said flexible portion having one end connected to an end of said rigid portion, said flexible portion having an opposite end connected to said recoil means, said flexible portion of said needle assembly comprising:
a bead;
a flexible line being connected to said recoil means and extending through said bead;
a first rigid spacer member affixed to said end of said rigid portion of said needle assembly; and
a plurality of additional rigid spacers interposed in jointed relationship between said first rigid spacer and said bead.
2. The assembly of claim 1, said rigid portion of said needle assembly having an extended position extending outwardly of said outlet extension of said housing.
3. The assembly of claim 2, said rigid portion of needle assembly extending in generally tangential relationship to said rounded area of said housing when in said extended position.
4. The assembly of claim 2, said rigid portion having a length of approximately two inches.
5. The assembly of claim 1, said trigger means being a slide member, said slide member capturing said bead of said flexible portion of said needle assembly, said trigger means for releasing said bead so as to cause said recoil means to retract.

6. The assembly of claim 5, said slide member positioned in said outlet extension of said housing, said slide member having a portion extending outwardly of said housing so as to be movable by an index finger of a human being.

7. The assembly of claim 1, said flexible line selected from a group consisting of a cord, a nylon line, and a wire.

8. The assembly of claim 1, said housing having a size suitable for fitting between a thumb and a index finger of a human being.

9. The assembly of claim 1, said recoil means comprising:
   a spool rotatably positioned within said interior area of said housing in said rounded area; and
   a constant force spring cooperative with said spool so as to urge said spool to rotate in a single direction.

10. A catheter housing assembly comprising:
    a housing having a generally rounded area and having a outlet extension extending outwardly of said rounded area, said housing having an interior area;
    a needle assembly having a rigid portion and a flexible portion, said rigid portion of said needle assembly having an extended position extending outwardly of said outlet extension of said housing, said flexible portion having one end connected to an end of said rigid portion;
    a recoil means positioned in said interior of said housing, said recoil means for coiling said flexible portion of said needle assembly therearound, said flexible portion of said needle assembly having an opposite end connected to said recoil means; and
    a trigger means connected to said housing and cooperative with said needle assembly so as to actuate said recoil means for retracting said rigid portion of said needle assembly into said interior area of said housing as said flexible portion of said needle assembly is coiled by recoil means, said flexible portion of said needle assembly comprising:
    a bead;
    a flexible line being connected to said recoil means and extending through said bead;
    a first rigid spacer member affixed to said end of said rigid portion of said needle assembly; and
    a plurality of additional rigid spacers interposed in jointed relationship between said first rigid spacer member and said bead.

11. The assembly of claim 10, said trigger means being a slide member, said slide member capturing said bead of said flexible portion of said needle assembly, said trigger means for releasing said bead so as to cause said recoil means to retract said needle assembly.

12. The assembly of claim 11, said slide member positioned in said outlet extension of said housing, said slide member having a portion extending outwardly of said housing so as to be movable by an index finger of a human being grasping said housing.

13. The assembly of claim 10, said recoil means comprising:
    a spool rotatably positioned in said interior area of said housing in said rounded area; and
    a constant force spring cooperative with said spool so as to urge said spool to rotate in a single direction.

* * * * *